US012502149B2

(12) United States Patent
St. Pierre et al.

(10) Patent No.: US 12,502,149 B2
(45) Date of Patent: *Dec. 23, 2025

(54) BREAST COMPRESSION AND IMAGING SYSTEMS AND METHODS

(71) Applicant: Hologic, Inc., Marlborough, MA (US)

(72) Inventors: Shawn St. Pierre, The Hills, TX (US); Alan Rego, Woodbury, CT (US); Richard Gladwin Edwards, Brookfield, CT (US); Joseph Vartolone, Danbury, CT (US); Timothy Wells, Manchester, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,008

(22) Filed: Apr. 23, 2024

(65) Prior Publication Data

US 2024/0341703 A1 Oct. 17, 2024

Related U.S. Application Data

(63) Continuation of application No. 18/195,176, filed on May 9, 2023, now Pat. No. 11,998,371, which is a (Continued)

(51) Int. Cl.

*A61B 5/00* (2006.01)
*A61B 6/04* (2006.01)

(Continued)

(52) U.S. Cl.

CPC .......... *A61B 6/0414* (2013.01); *A61B 6/0435* (2013.01); *A61B 6/0492* (2013.01); *A61B 6/461* (2013.01); *A61B 6/502* (2013.01)

(58) Field of Classification Search

CPC ......... A61B 6/482; A61B 6/545; A61B 6/502; A61B 6/463; A61B 6/4035; A61B 6/5217;

(Continued)

(56) References Cited

U.S. PATENT DOCUMENTS

| | | | |
|---|---|---|---|
| 5,335,257 | A | 8/1994 | Thunberg |
| 11,357,456 | B2 | 6/2022 | St. Pierre |

(Continued)

FOREIGN PATENT DOCUMENTS

| | | | |
|---|---|---|---|
| CN | 105611876 | A | 5/2016 |
| EP | 2747659 | | 7/2014 |

(Continued)

OTHER PUBLICATIONS

European Extended Search Report in Application 22183199.3, mailed Jan. 5, 2023, 11 pages.

(Continued)

*Primary Examiner* — Don K Wong
(74) *Attorney, Agent, or Firm* — Merchant & Gould P.C.

(57) ABSTRACT

A compression paddle with a plurality of markers is advanced towards a patient's breast which has been positioned on a support platform for an imaging procedure. An initial position of the compression paddle is detected relative to the support platform when a portion of the breast is contacted. An initial marker is identified which is associated with a feature of the breast when the compression paddle is in the initial position. A compression target marker is based at least in part on the initial position and the initial marker.

18 Claims, 10 Drawing Sheets

Related U.S. Application Data continuation of application No. 17/744,975, filed on May 16, 2022, now Pat. No. 11,701,068, which is a continuation of application No. 16/981,362, filed as application No. PCT/US2019/033570 on May 22, 2019, now Pat. No. 11,357,456.

(60) Provisional application No. 62/676,472, filed on May 25, 2018.

(51) Int. Cl.
*A61B 6/46* (2024.01)
*A61B 6/50* (2024.01)

(58) Field of Classification Search
CPC .. A61B 6/488; A61B 6/54; A61B 6/46; A61B 6/08
See application file for complete search history.

(56) References Cited

U.S. PATENT DOCUMENTS

| | | | |
|---|---|---|---|
| 11,701,068 B2 | 7/2023 | St. Pierre | |
| 2009/0262887 A1 | 10/2009 | Iordache | |
| 2009/0268865 A1* | 10/2009 | Ren | A61B 6/0414 378/37 |
| 2011/0305313 A1 | 12/2011 | Sklansky et al. | |
| 2014/0226786 A1 | 8/2014 | Goosen et al. | |
| 2014/0301529 A1 | 10/2014 | Ren et al. | |
| 2014/0328458 A1 | 11/2014 | Erhard et al. | |
| 2015/0297163 A1 | 10/2015 | Kim et al. | |
| 2016/0166222 A1 | 6/2016 | Kim | |
| 2016/0235379 A1 | 8/2016 | Homann | |
| 2017/0367671 A1 | 12/2017 | Arai et al. | |
| 2017/0367675 A1 | 12/2017 | Arai et al. | |
| 2019/0000318 A1 | 1/2019 | Caluser | |
| 2020/0188056 A1 | 6/2020 | Livingston | |
| 2023/0329652 A1 | 10/2023 | St. Pierre | |

FOREIGN PATENT DOCUMENTS

| | | |
|---|---|---|
| JP | H02-086100 A | 3/1990 |
| JP | H06-154194 | 6/1994 |
| JP | 2009-285345 | 12/2009 |
| JP | 2014-057901 A | 4/2014 |
| JP | 2014-527870 A | 10/2014 |
| JP | 2016-515436 A | 5/2016 |
| JP | 2016-535622 A | 11/2016 |
| JP | 2017-502596 A | 1/2017 |
| JP | 2017-225635 A | 12/2017 |
| WO | 03/037046 | 5/2003 |
| WO | 2014/167097 | 10/2014 |
| WO | 2015/062903 | 5/2015 |

OTHER PUBLICATIONS

PCT International Preliminary Report on Patentability in Application PCT/US2019/033570, mailed Dec. 10, 2020, 10 pages.
PCT International Search Report and Written Opinion of the International Searching Authority for International Patent Application No. PCT/US2019/033570 dated Nov. 20, 2019, 16 pages.

* cited by examiner

BREAST COMPRESSION AND IMAGING SYSTEMS AND METHODS

CROSS-REFERENCE TO RELATED APPLICATIONS

This application is a continuation of U.S. patent application Ser. No. 18/195,176, now U.S. Pat. No. 11,998,371, filed May 9, 2023, which is a continuation of U.S. patent application Ser. No. 17/744,975, now U.S. Pat. No. 11,701,068, filed May 16, 2022, which is a continuation of U.S. patent application Ser. No. 16/981,362, now U.S. Pat. No. 11,357,456, filed Sep. 16, 2020, which application is a National Stage Application of PCT/US2019/033570, filed May 22, 2019, which claims priority to U.S. Provisional Patent Application No. 62/676,472, filed May 25, 2018, the entire disclosures of which are hereby incorporated herein by reference.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technician or other health professional is holding the breast in place. The technician may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to a method of compressing a breast for an imaging procedure, the method including: advancing a compression paddle towards the breast positioned on a support platform, wherein the compression paddle has a plurality of markers disposed thereon; contacting at least a portion of the breast with the compression paddle; detecting, based on the contacting, an initial position of the compression paddle relative to the support platform; identifying an initial marker of the plurality of markers, wherein the initial marker is associated with a feature of the breast when the compression paddle is in the initial position; and determining a compression target marker of the plurality of markers based at least in part on the initial position and the initial marker. In an example, the method further includes terminating compression of the breast when the feature of the breast is associated with the compression target marker. In another example, the method further includes, after the determining operation: initiating a target compression of the breast; monitoring a condition of the breast; and terminating the target compression when the condition reaches a predetermined condition. In yet another example each of the plurality of markers are positioned on the compression paddle at a plurality of distances from a leading edge of the compression paddle. In still another example, the plurality of markers include automatic exposure markers.

In another example of the above aspect, the identifying operation includes activating at least one of a laser sensor, a time-of-flight sensor, and an optical sensor from a location opposite the compression paddle from the breast. In an example, the feature of the breast has at least one of a nipple, a skin line, a chest wall, and an axilla tissue. In another example, the determining operation includes comparing at least one of the initial marker and the initial position to a test dataset.

In another aspect, the technology relates to a method of compressing a breast with a compression paddle of an imaging system, the method including: scanning at least a portion of the breast to determine an initial condition of the breast; initiating a compression of the breast with the compression paddle, wherein the breast is compressed against a support platform; monitoring a change condition of the breast; and terminating the compression operation when the change condition reaches a predetermined condition. In an example, the change condition is associated with at least one of a change in a width and a shape of the breast. In another example, the scanning operation and monitoring operation each include activating a sensor having at least one of a laser sensor, a time-of-flight sensor, and an optical sensor, wherein the sensor emits a signal into a volume at least partially defined by the breast platform and the compression paddle. In yet another example, the method further includes determining a position of an x-ray receptor disposed proximate the support platform. In still another example, the determining operation includes receiving a signal from a position sensor associated with the x-ray receptor.

In another example of the above aspect, the determining operation further includes associating the position signal with at least one of a width and a profile of the breast. In an example, the method further includes displaying, on a screen associated with the imaging system, a representation of the x-ray receptor and the breast relative to the x-ray receptor. In yet another example, the method further includes displaying a representation of an imaging target on the screen.

In another aspect, the technology relates to a method of determining a condition of a breast for an imaging procedure, the method including: compressing the breast between a movable compression paddle and a support platform; monitoring a position of at least a portion of the compression paddle relative to the support platform; emitting a signal towards the a feature disposed on the compression paddle; receiving a return signal from the feature in response to the emitted signal; and determining a flexure of the compression paddle based at least in part on the return signal. In an example, the method further includes calculating a dose to be delivered to the breast based at least in part on the position and the flexure. In another example, the method further includes determining if at least one of the position and the flexure meets a predetermined criteria; and terminating the compression operation based on the predetermined criteria determination. In yet another example, the emitted signal includes at least one of a laser signal, an optical signal, and a time-of-flight signal. In still another example, the feature includes a machine-readable feature.

In another example of the above aspect, the return signal includes the emitted signal reflected by the feature. In an example, the feature is disposed on a substantially vertical portion of the compression paddle.

DETAILED DESCRIPTION

Figure 1A:
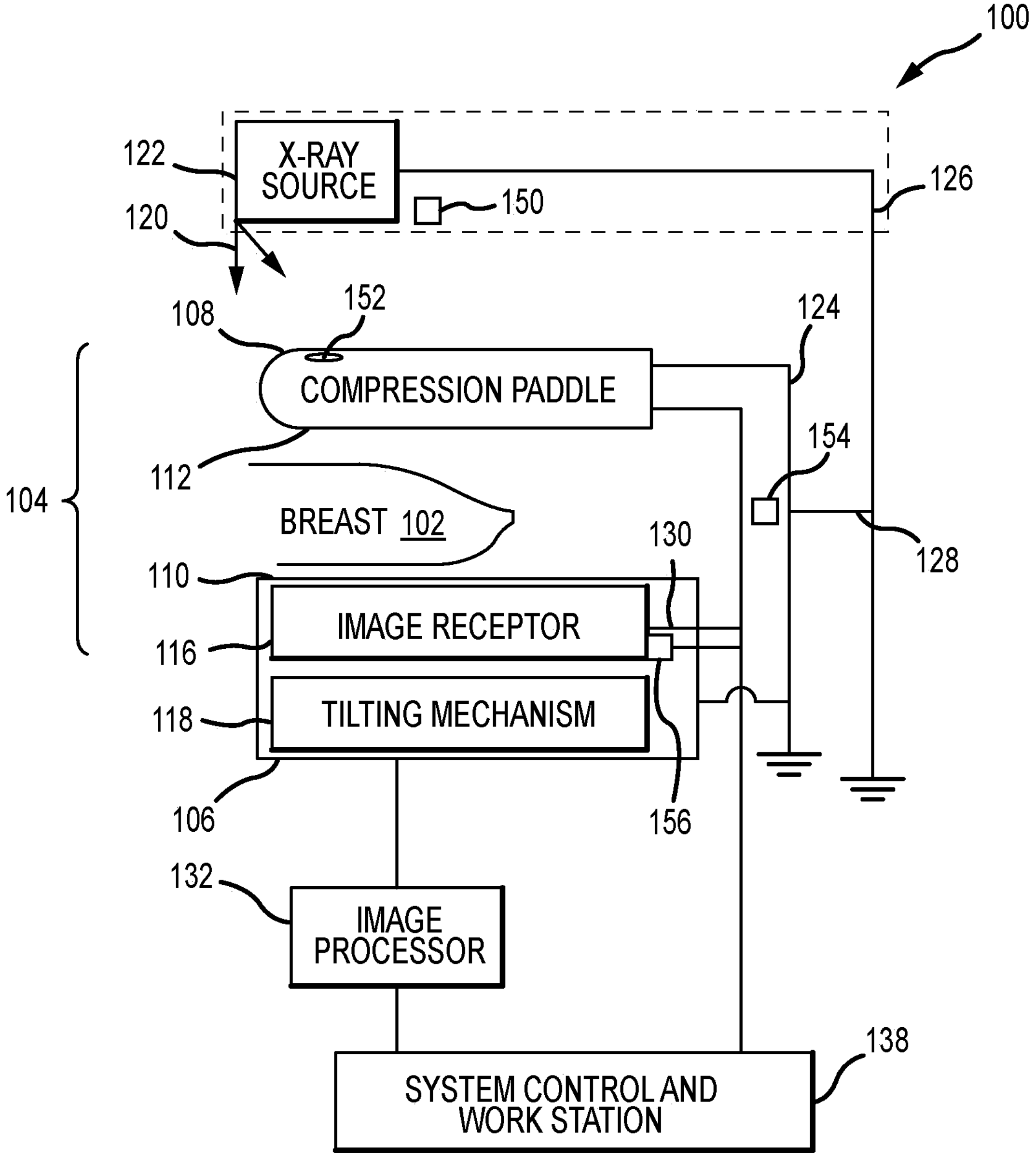
FIG. 1A is a schematic view of an exemplary imaging system.
Figure 1B:
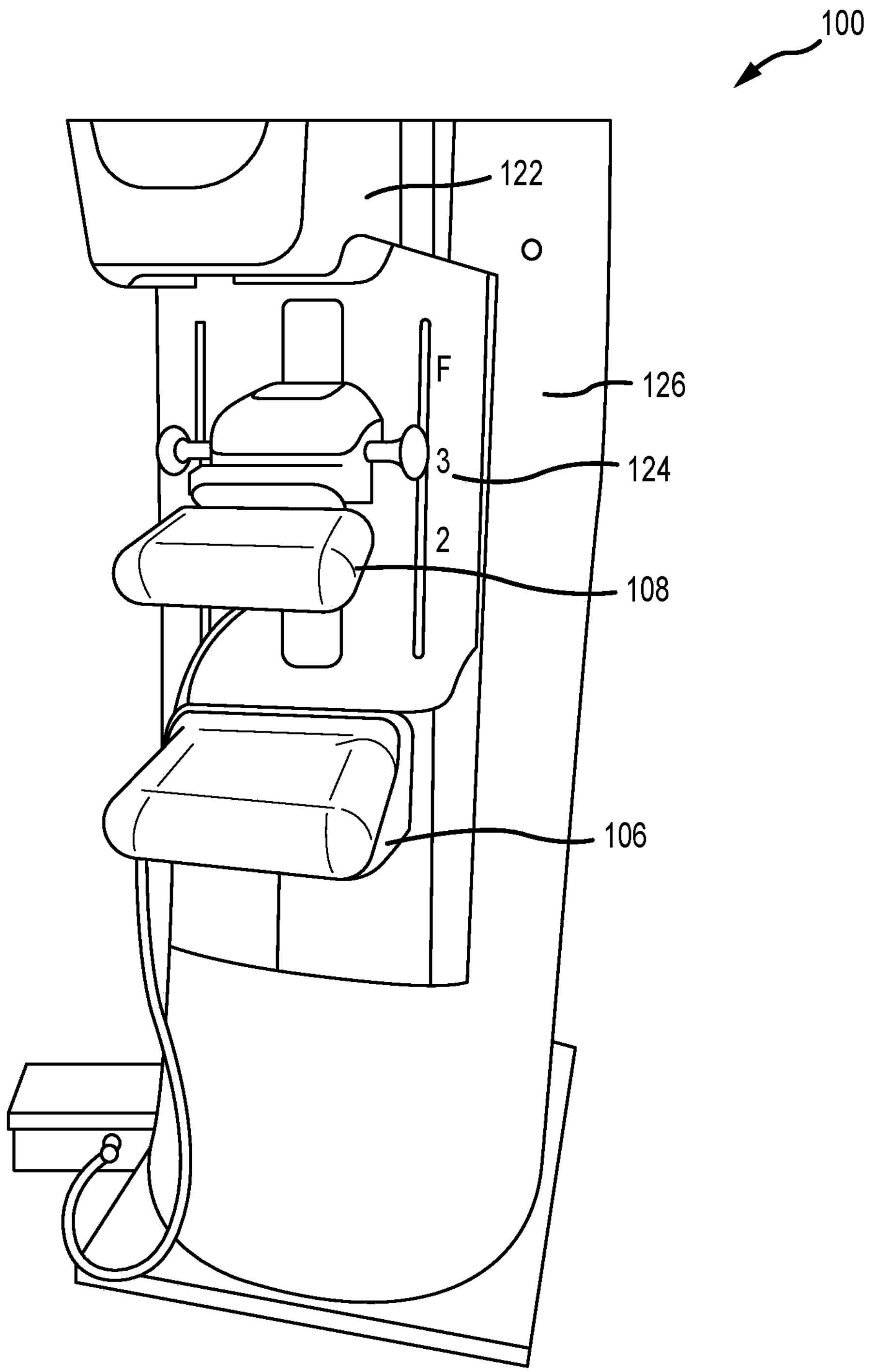
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit or compression system 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118. The immobilizer unit 104 is in a path of an imaging beam 120 emanating from x-ray source 122, such that the beam 120 impinges on the image receptor 116.

The compression system 104 is supported on a first support arm 124 and the x-ray source 122 is supported on a second support arm, also referred to as a tube arm 126. For mammography, support arms 124 and 126 can rotate as a unit about an axis 128 between different imaging orientations such as cranial-caudal (CC) and mediolateral oblique (MLO) views, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the tube arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102. As such, the compression system 104 and tube arm 126 may be rotated discrete from each other, unless matched rotation is required or desired for an imaging procedure.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. As the compressive pressure applied by the paddle to the breast is increased, the patient may experience discomfort.

The technologies described herein relate to a breast compression and imaging system that utilizes a number of sensors to monitor conditions of the breast and/or breast paddle so as to help reduce discomfort associated with compression. In examples, the technologies described herein help ensure that the breast is sufficiently immobilized for imaging, without being overly compressed. Still other technologies may improve the accuracy or measurement of forces applied to the breast, thus providing feedback to a technologist, thereby allowing them to ensure sufficient immobilization for proper imaging. The technologies described herein utilize sensors that measure distance or proximity to the breast, or that detect changes in features, shapes, or other characteristics or conditions of the breast. By using such sensors to monitor the breast before and/or during compression, the technician is able to identify when an applied compressive force does not further significantly compress the breast; at this point, further applied compressive force simply increases patient discomfort, often with no medically relevant benefit. Further, use of the sensor systems described herein may automate and ensure consistent immobilization of the breast without full compression without necessarily relying upon the judgment, skill, or experience of a technologist. Sensors utilized may include those that emit laser light in the visible or invisible spectrums, time-of-flight (ToF) cameras or sensors, light detection and ranging (LIDAR) sensors, motion sensing systems, optical sensors, and so on. Such sensors are depicted in exemplary locations in FIG. 1A.

Imaging systems including any one of the sensors that perform the functions described herein are contemplated, although certain systems may include all of the described sensors, or additional sensors that are positioned differently but that perform the various functions described herein. In certain examples, the sensors described herein may perform a single described function or a plurality of functions. Additionally, "sensors" as described herein, may include devices that both emit and receive signals to perform the sensing functions described (e.g., a transceiver). In other examples, the term "sensor" may refer to a sensor discrete from an associated emitter, but communicatively coupled to the emitter so as to operate effectively as a single component.

Returning to FIG. 1A, a number of sensors are depicted in various locations of the imaging system. A tube head sensor 150 is depicted on the tube head 126. The tube head sensor 150 generally points downward towards the compression paddle 108, breast 102, and the support platform 106. Functions performed in conjunction with the tube head sensor 150 are described herein and may include: detecting flexure of the compression paddle 108 (for example, in conjunction with a feature 152 thereon), and/or detecting a condition of the breast 102 prior to or during compression. A compression system sensor 154 is disposed on the compression system 104 and generally points forward toward the breast 102. Functions performed in conjunction with the compression system sensor 154 are described herein and may include detecting a condition or position of the breast 102 prior to or during compression. A position sensor 156, for example, in the form of an encoder, is associated with the image receptor 116 so as to detect a position thereof. The position sensor 156 may be used in conjunction with the other sensors 150, 154 to aid in determining a position of the breast 102 relative to the image receptor 116. Additional sensors are also depicted and described herein.

Figure 2A:
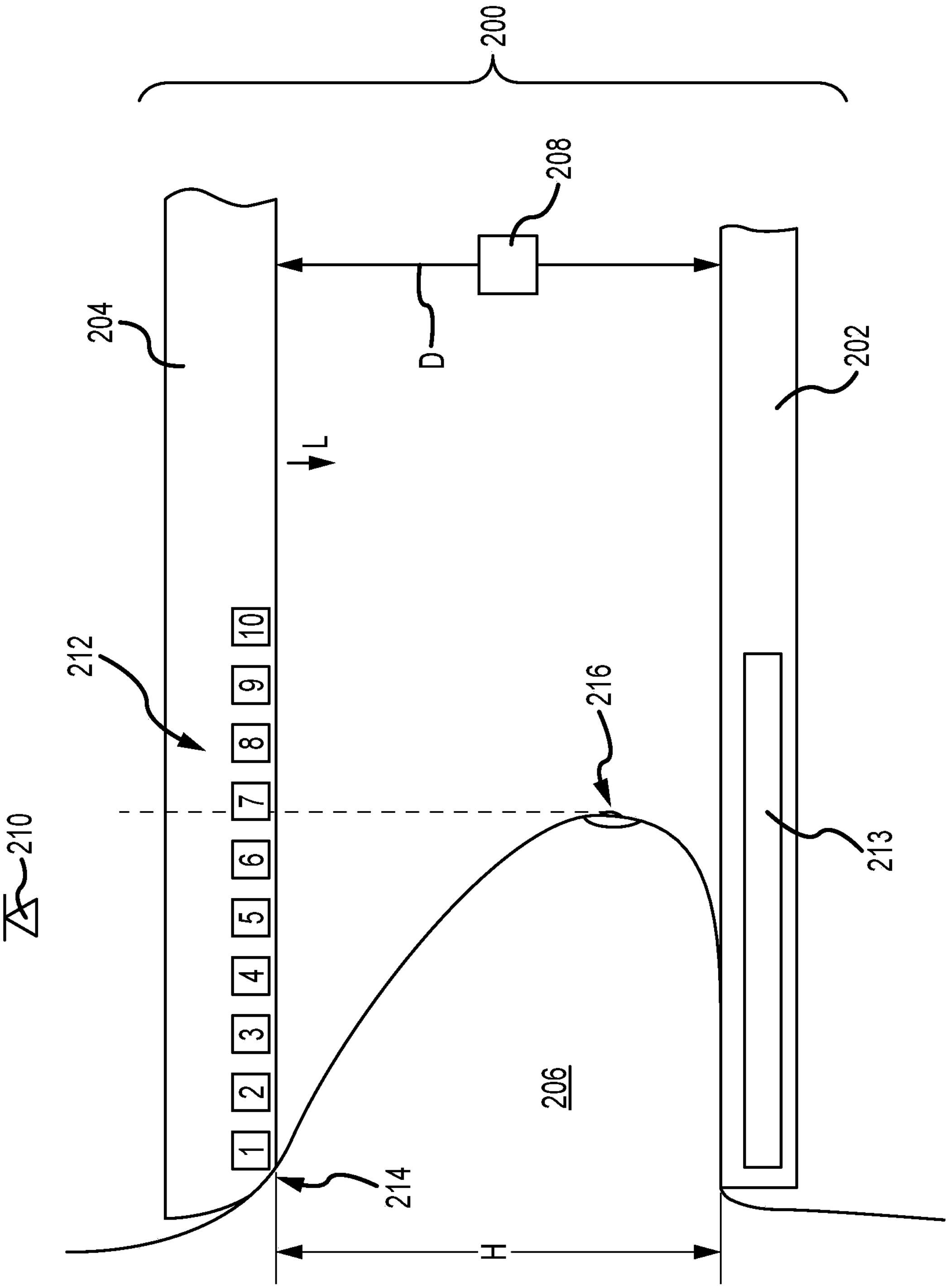
FIGS. 2A-2B are schematic views of a breast compression system in a plurality of positions.
Figure 2B:
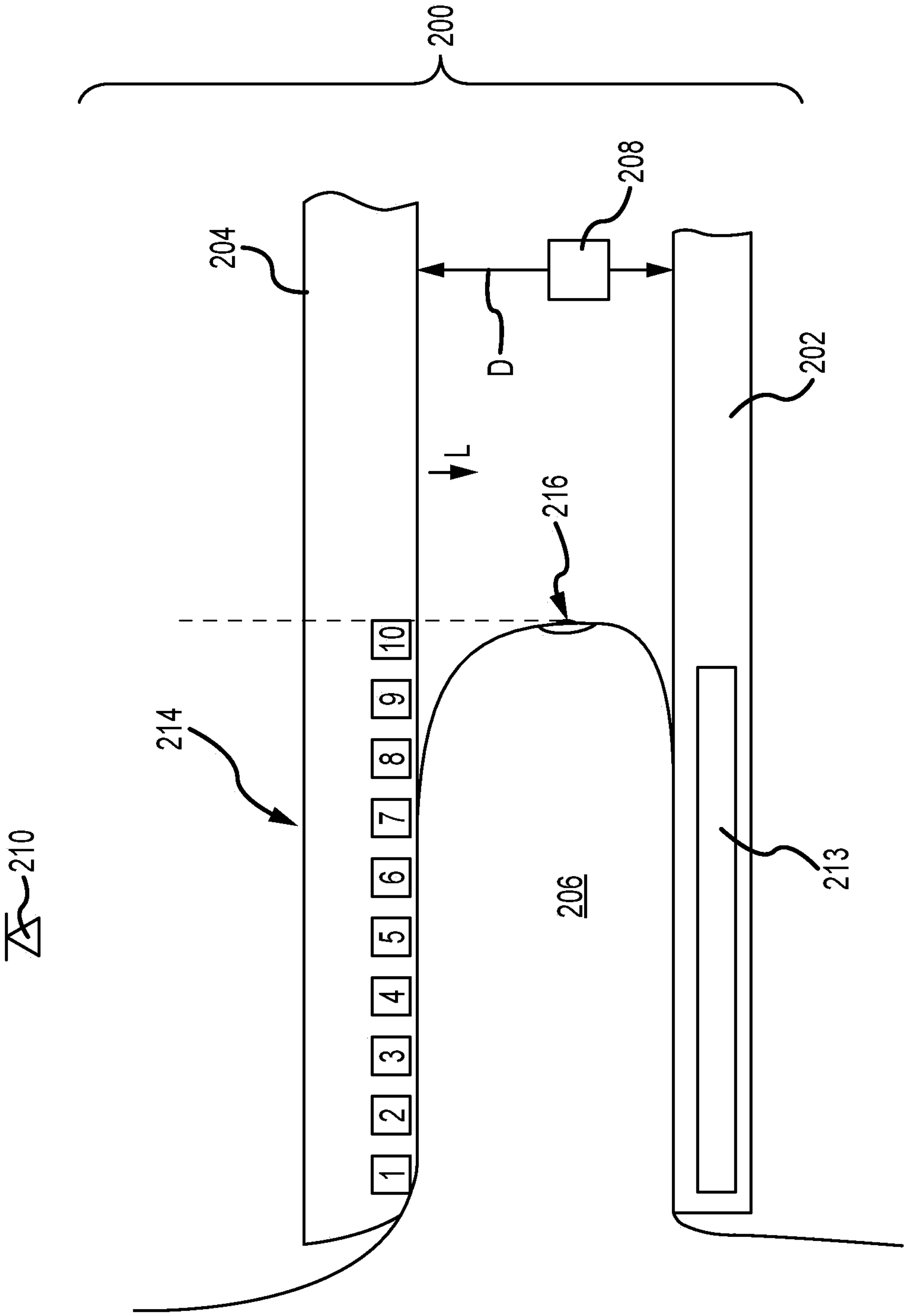

FIGS. 2A-2B are schematic views of a breast compression system 200 in a plurality of positions and are described generally concurrently. As noted above, the breast compression system 200 includes a breast support platform 202 and a movable breast compression paddle 204. A breast 206 is disposed between the support platform 202 and compression paddle 204 in advance of an imaging procedure. A position encoder 208 that measures the distance D between the support platform 202 and the compression paddle 204 is also depicted, and may be disposed on a different component of the compression system 200; a number of appropriate components are contemplated. Breast imaging systems typically utilize such position encoders to determine, e.g., the distance from the support platform 202 to the compression paddle 204. Thus, the encoder 208 detects the distance D as the compression paddle 202 is lowered. FIG. 2A also depicts a sensor 210 mounted, for example, on the tube head (not shown). The compression paddle 204 also includes a plurality of markers 212 (e.g., so-called automatic exposure control (AEC) markers). The markers 212 are aligned with AEC detectors (not shown) disposed in the x-ray receptor 213 in the breast platform 202. The detectors receive x-ray dosage during imaging procedures; procedures are terminated when a predetermined amount of dose has been received, as known in the art. In practice, the AEC markers 212 on the compression paddle 204 are used by a technician to identify an appropriate AEC detector (as related to a position of the breast 206) to control the dosage given to the patient.

In the compression system 200 depicted in FIGS. 2A and 2B, the tube head sensor 210, in conjunction with the AEC markers 212 and compression paddle encoder 208, is used to determine the amount of compression required to properly compress the breast 206. FIG. 2A depicts an initial condition of the compression system 200 for making this compression determination. As the compression paddle 204 is lowered, the compression paddle 204 contacts the breast 206 at an initial contact point (depicted in this example as location 214). This contact may be detected in a number of ways. In an example, the compression paddle encoder 208 may detect a change in rate of movement. In another example, a strain gauge located on the compression paddle 204 or on another component of the compression system 200 may detect a loading of the compression paddle 204. In yet another example, a change in a load on the motor that lowers the compression paddle 204 may be detected. Regardless of how the contact is detected, the encoder 208 sends an associated signal to a controller which may use the signal to determine the distance D between the compression paddle 204 and the support platform 202. Also at initial contact, the tube head sensor 210 detects a position of the breast 206 relative to the individual AEC markers 212 to determine an initial marker. In this case, the tube head sensor 210 can identify an alignment between a feature of the breast 206 (for example, the nipple 216) and a particular AEC marker 212 (in this case, marker #7). With a known initial positon of the compression paddle 204 and initial marker 212, characteristics of the breast (e.g., volume, uncompressed height H, etc.) may be determined or approximated.

Based on these determinations, the compression system 200, or a program associated with the imaging system or a remote computer, may determine a target AEC marker. In this example, target marker 212 (target marker #10) is identified, based on known datasets (e.g., test results of known breasts of various dimensions). The target marker 212 corresponds generally to a compressed position of the breast 206 appropriate for imaging. Lowering L (e.g., compression) of the compression paddle 204 continues until the tube head sensor 210 identifies an alignment between the feature 216 with the target marker #10. Thus, the function of identifying target markers is utilized as a surrogate for an applied compressive force. As such, the compression paddle 204 need only compress the breast 206 until the proper breast configuration is obtained as detected by the tube head sensor 210. This may prevent over compression of the breast 206, which may occur if a target compressive force is instead utilized to stop the compression. The method described above with regard to FIGS. 2A and 2B is described in greater detail herein.

Figure 3A:
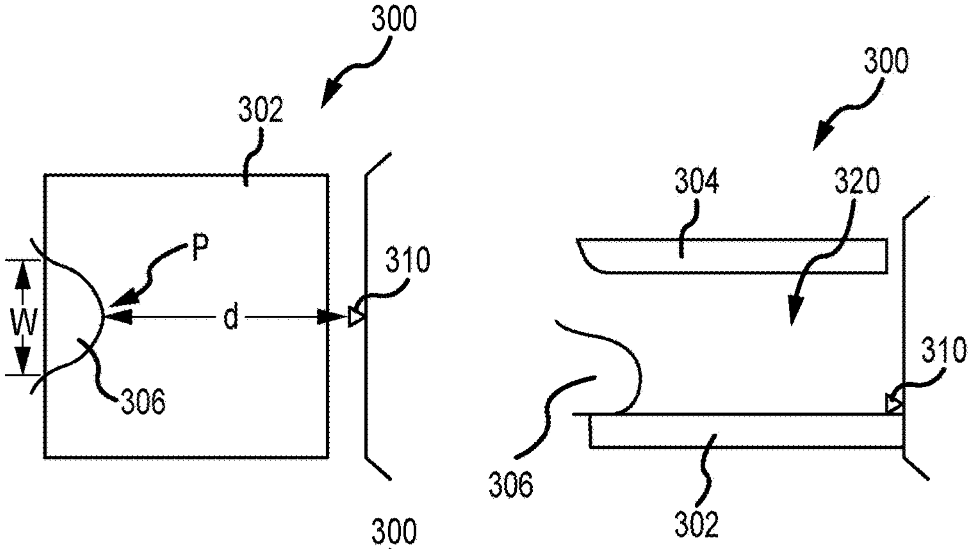
FIGS. 3A-3C are top schematic and side schematic views of a compression system in three positions.
Figure 3B:
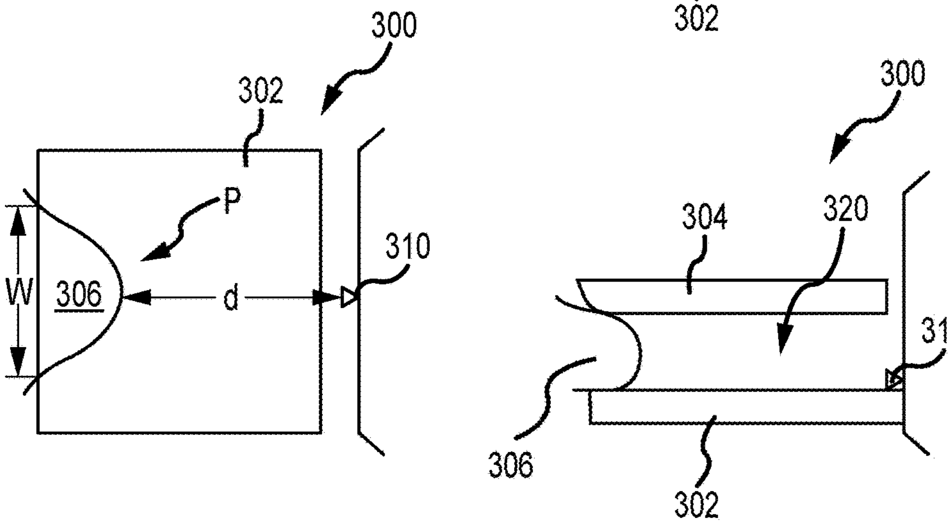
Figure 3C:
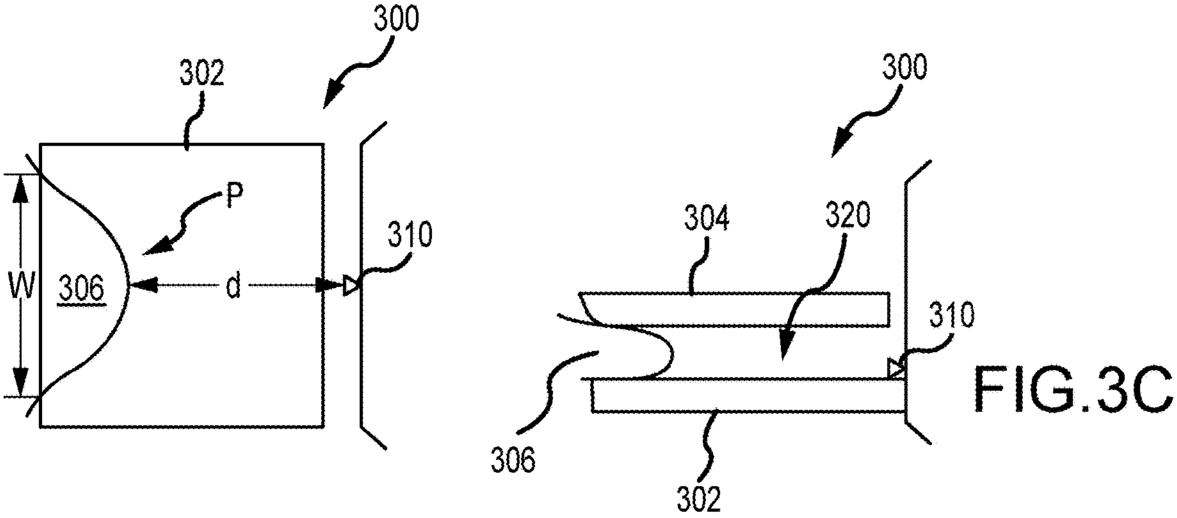

FIGS. 3A-3C are top schematic (left) and side (right) schematic views of a compression system 300 in three positions. This configuration enables another method of compressing a breast 306, as features of that breast 306 are detected by a sensor (in this case, a compression system sensor 310). Like the system described above in FIGS. 2A and 2B, the compression system 300 may utilize the sensor 310 to detect a compression of the breast 306. The compression system 300 includes again a support platform 302 and a movable compression paddle 304. The compression system sensor 310 is directed into a volume 320 defined at least partially by the support platform 302 (below) and the compression paddle 304 (above). In the top schematic of each of FIGS. 3A-3C, the compression paddle 304 is not depicted for clarity. In FIG. 3A, the compression paddle 304 is not in contact with the breast 306, as clear from the side schematic view. The breast 306 rests on the support platform 302. The sensor 310 may detect a number of conditions of the breast 306. For example, a width w, distance d to the sensor 310, or profile P shape may be detected. As the compression paddle 304 is lowered and compressed against the breast 306, operation of the sensor 310 continues, and thus a change in one or more of the conditions of the breast 306 is detected. As compression increases, any one or all of the breast maximum width w, distance d to sensor 310, or profile P shape may change. The data received by the sensor 310 may be compared to known or test data and used to calculate a force applied to the breast 306. In another example, compression of the breast 306 may continue until a change in condition meets a threshold. Such a threshold may include a reduction in or termination of a rate of change of the condition in response to further compression. In an example, this may be indicative of no further flattening of the breast 306, notwithstanding the application of additional compressive force.

In another example, a tube head sensor may be utilized in lieu of, or in addition to, the compression system sensor 310 to obtain much of the same results. When using the tube head sensor, it may be advantageous to utilize an optical sensor, or a sensor that otherwise emits signals that may penetrate the transparent or translucent compression paddle 304. Regardless, any sensor utilized may project a grid or other visible pattern onto the breast to aid in, e.g., mapping contours or a profile of the breast 306, identifying features on the breast, and so on.

Figure 4:
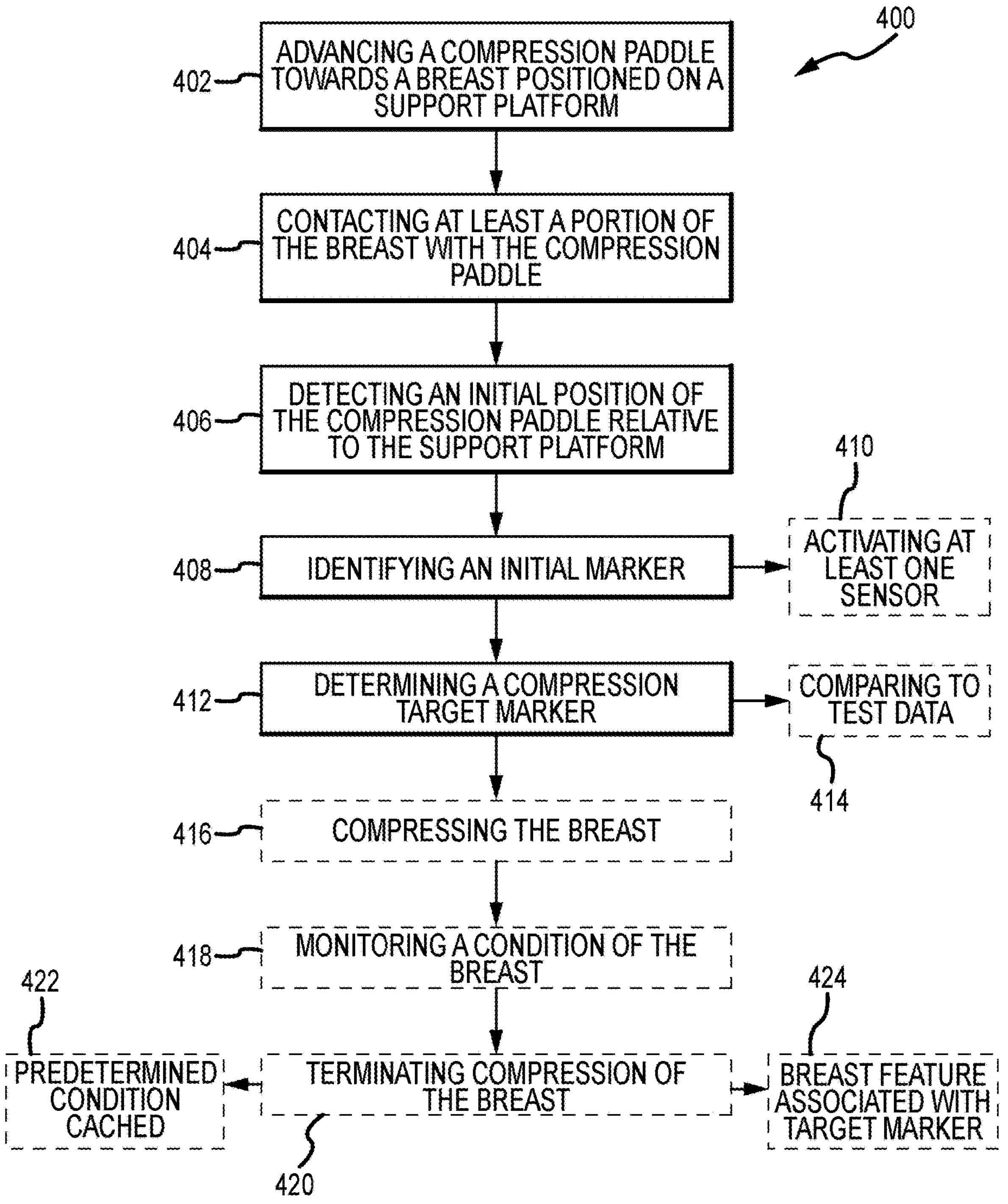
FIG. 4 depicts a method of compressing a breast in an imaging system.

FIG. 4 depicts a method 500 of compressing a breast in an imaging system. The method 400 may be further understood in the context of FIGS. 2A and 2B. In general, the method 400 contemplates using initial conditions of a breast, prior to compression, to determine, predict, or approximate a target condition of a breast that would be appropriate for imaging. Data obtained from various sensors on the imaging system are compared to known data from prior compressions, similar breasts, or similar procedures to identify an appropriate target compression. As such, the method 400 reduces or entirely obviates the need to compress the breast to a point of discomfort. The method 400 begins with operation 402, advancing a compression paddle towards the breast positioned on a support platform. The compression paddle may include a plurality of markers disposed thereon, for example, the AEC markers depicted in FIGS. 2A and 2B. AEC markers are particularly useful because they are positioned on the compression paddle at various known distances from a leading edge of the paddle. These distances, and the AEC markers associated therewith, are aligned with known AEC detectors on the x-ray receptor. In operation 404, at least a portion of the breast is contacted with the compression paddle. Based on that contact, an initial position of the compression paddle relative to the support platform is detected in operation 406. In operation 408, an initial marker of the plurality of markers is identified. This initial marker is associated with a feature of the breast when the compression paddle is in the initial position. This feature may be a marker placed on the breast (e.g., by a technician), or may be a mark resulting from a previous breast procedure (e.g., a scar from a biopsy or lumpectomy), or may be a natural feature of the breast (e.g., a mole or nipple). The association may include identifying a marker of the plurality of markers that is aligned or adjacent to the feature of the breast. In an example, the identifying operation 408 may include activating at least one of a laser sensor, a time-of-flight sensor, and an optical sensor from a location opposite the compression paddle from the breast, such as depicted in optional operation 410. Such types of sensors are described elsewhere herein and may be disposed on a number of components of the imaging system. In operation 412, a compression target marker of the plurality of markers is determined based at least in part on the initial position and the initial marker. In general, the compression target marker may be determined by comparing information already obtained (e.g., the initial position and the initial marker) to known comparable information. The comparison to known information allows the compression system to apply an appropriate amount of compressive force to the breast so as to attain an appropriate amount of compression for imaging. Such known information may be test data from prior compressions of similar breasts, as depicted in operation 414, to which the initial position and initial marker are compared.

Compression of the breast begins at operation 416, in an effort to associate the feature of the breast with the target marker. During compression, a condition (e.g., a width, position, or distance such as described elsewhere herein), may be monitored (operation 418), for example, by the sensors described herein. This compression may be terminated (operation 420) for any number of reasons. For example, operation 422 contemplates terminating compression when a predetermined condition of the breast is reached. This predetermined condition may be a maximum condition (e.g., a width) or a minimum condition (compressed thickness). The predetermined condition may be a rate change of a condition. For example, a breast that, upon application of a compressive force, no longer deforms or gets thinner may be considered to have met the predetermined condition. In another example, depicted in operation 424, compression may be terminated when the breast feature is associated with (e.g., aligns) with the target marker. Thereafter, imaging may be performed.

Figure 5:
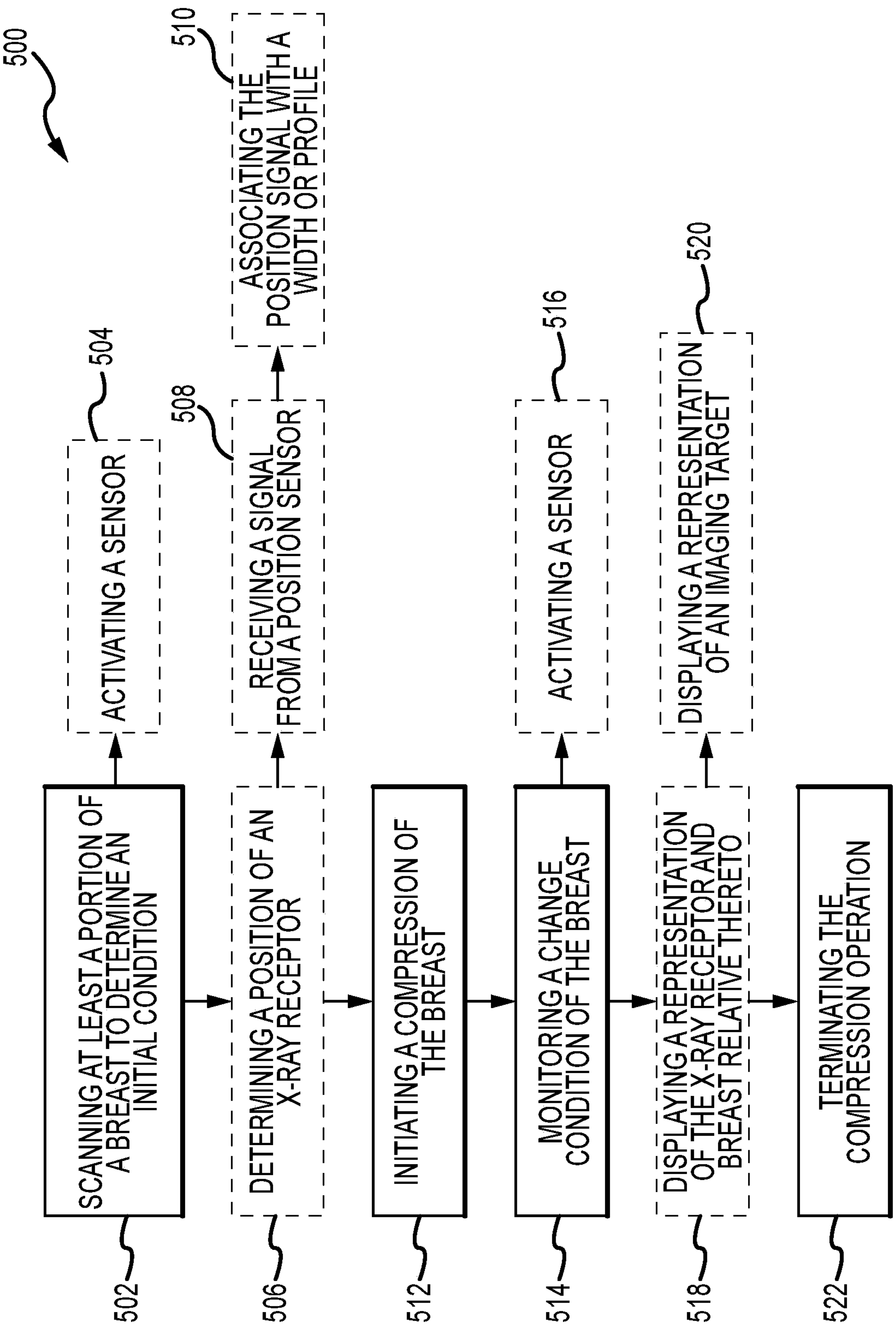
FIG. 5 depicts another method of compressing a breast in an imaging system.

FIG. 5 depicts another method 500 of compressing a breast in an imaging system. The method 500 may be further understood in the context of FIGS. 3A-3C. In general, the method 500 contemplates continually monitoring physical conditions of a breast during compression procedures. Such monitoring is used to properly position and compress a breast for proper imaging. Continual monitoring also enhances a technician's ability to not only position the breast, but to compress the breast to a comfortable, but clinically relevant, level of compression. The precise details detected by the various sensors generally allow for greater accuracy in both positioning and compression, enabling the technician to provide reassurance and comfort to the patient during an often anxiety-inducing medical procedure. As such, the method 500 has the potential to significantly improve patient experience. The method 500 begins at operation 502 with scanning at least a portion of the breast to determine an initial condition of the breast. This scanning operation 502 may include activating (operation 504) at least one of a laser sensor, a time-of-flight sensor, and an optical sensor into a volume at least partially defined by the compression paddle and the support platform. The breast condition may include one or more of a width, a position, a profile, or a distance from the breast to the sensor, such as described elsewhere herein. In optional operation 506, a position of an x-ray receptor disposed proximate the support platform is determined. By determining this position, other operations may be performed, as described below. The position may be determined in a number of ways. For example, as depicted in operation 508, a position sensor associated with the x-ray receptor may send a signal regarding the position. This signal would be received by the controller operating the imaging system, for example. In another example, the determining operation may also include associating the position signal with a width or a shape of a breast, operation 510.

In operation 512, compression of the breast between a compression paddle and a support platform is initiated. During compression, a change condition of the breast is monitored, operation 514. This monitoring operation may include activating (operation 516) at least one of a laser sensor, a time-of-flight sensor, and an optical sensor into a volume at least partially defined by the compression paddle and the support platform. Use of sensors may also enable additional functionality in an imaging system. Operation 518 includes displaying, on a screen associated with the imaging system, a representation of the x-ray receptor and the breast relative to the x-ray receptor. This may aid a technologist in positioning the breast. In another example, the displaying operation may also include displaying a representation of an imaging target on the screen, operation 520. In operation 522, compression is terminated when the change condition reaches a predetermined condition. This predetermined condition may be a maximum condition, a minimum condition, or a rate change of a condition as described above.

Figure 6:
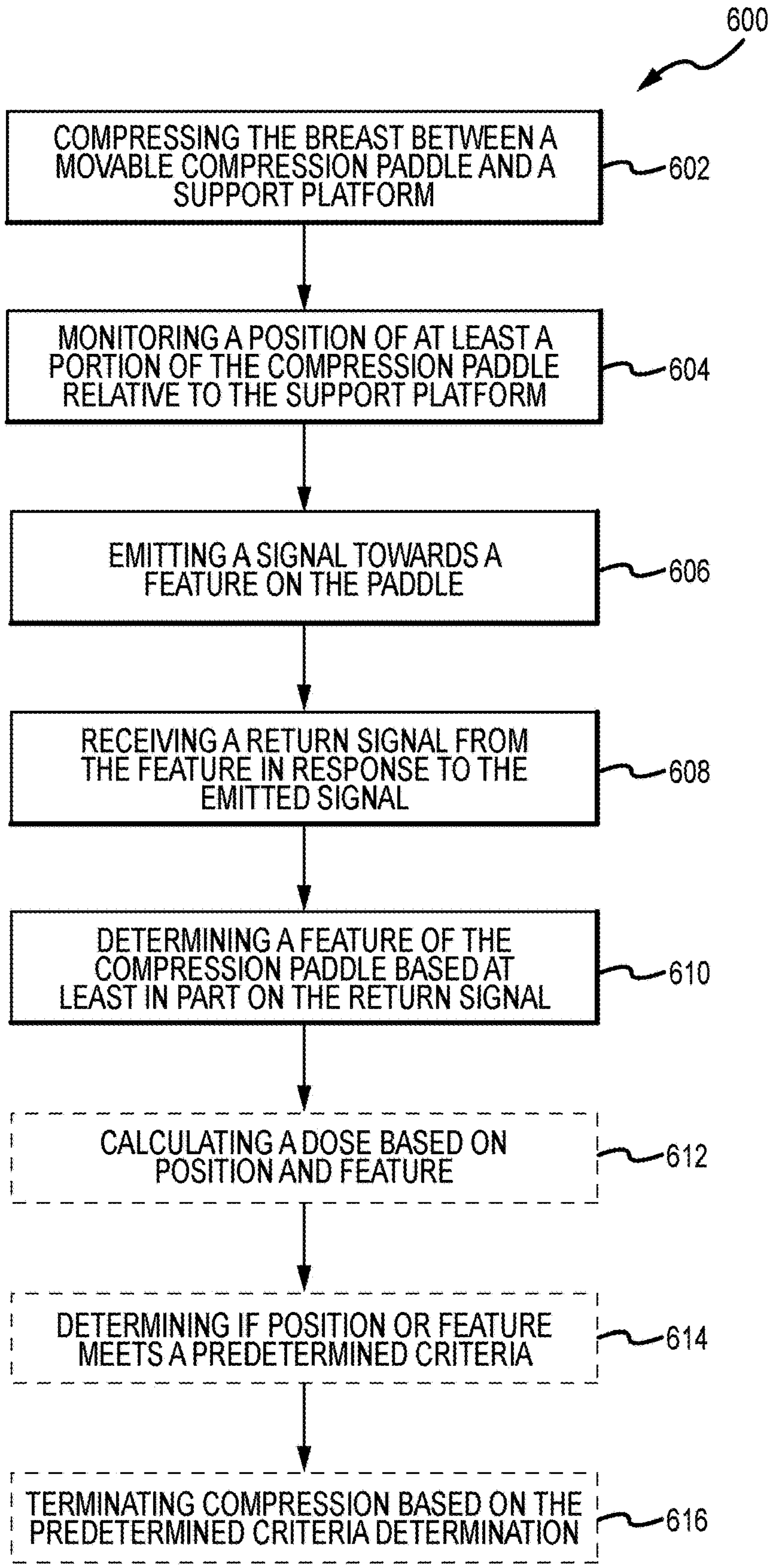
FIG. 6 depicts a method of determining a condition of a breast for an imaging procedure.

FIG. 6 depicts a method 600 of determining a condition of a breast for an imaging procedure. The method 600 may be further understood in the context of FIGS. 1A and 2A-2B. In general, the method 600 contemplates monitoring a distance between a compression paddle and a breast support platform. While such information has been used in prior art systems to determine the thickness of a compressed breast, the present method 600 utilizes further information (e.g., the detected flexure of the compression paddle) to obtain a more accurate measure of thickness of the compressed breast. The method 600 begins at operation 602, compressing the breast between a movable compression paddle and a support platform. A position of at least a portion of the compression paddle relative to the support platform is monitored in operation 604. Additionally, in operation 606, a signal is emitted towards a feature disposed on the compression paddle. The emitted signal may include at least one of a laser signal, an optical signal, and a time-of-flight signal, while the feature may be a machine-readable feature that in examples is disposed on a substantially vertical portion of the compression paddle. In another example, the feature may be disposed on a substantially horizontal portion of the compression paddle. In operation 608, a return signal is received from the feature in response to the emitted signal. In examples, the return signal is the emitted signal reflected by the feature. Based on the return signal, a flexure of the compression paddle may be determined, operation 610. With the flexure and paddle position information, optional operation 612 may be performed, which includes calculating a dose to be delivered to the breast based at least in part on the position and the flexure. Because the x-ray dose is based at least in part on the thickness of the breast, the position and flexure information enables a more accurate dose calculation. Further functionality is available with the depicted method 600. For example, operation 614 contemplates determining if at least one of the position and the flexure meets a predetermined criteria. Such criteria may include a change in a rate of flexure, or a position between the compression paddle and support platform that exceeds a threshold. Such thresholds may be indicative of an undesirable condition such as overcompression. Based on that predetermined criteria, further compression may be terminated.

Figure 7:
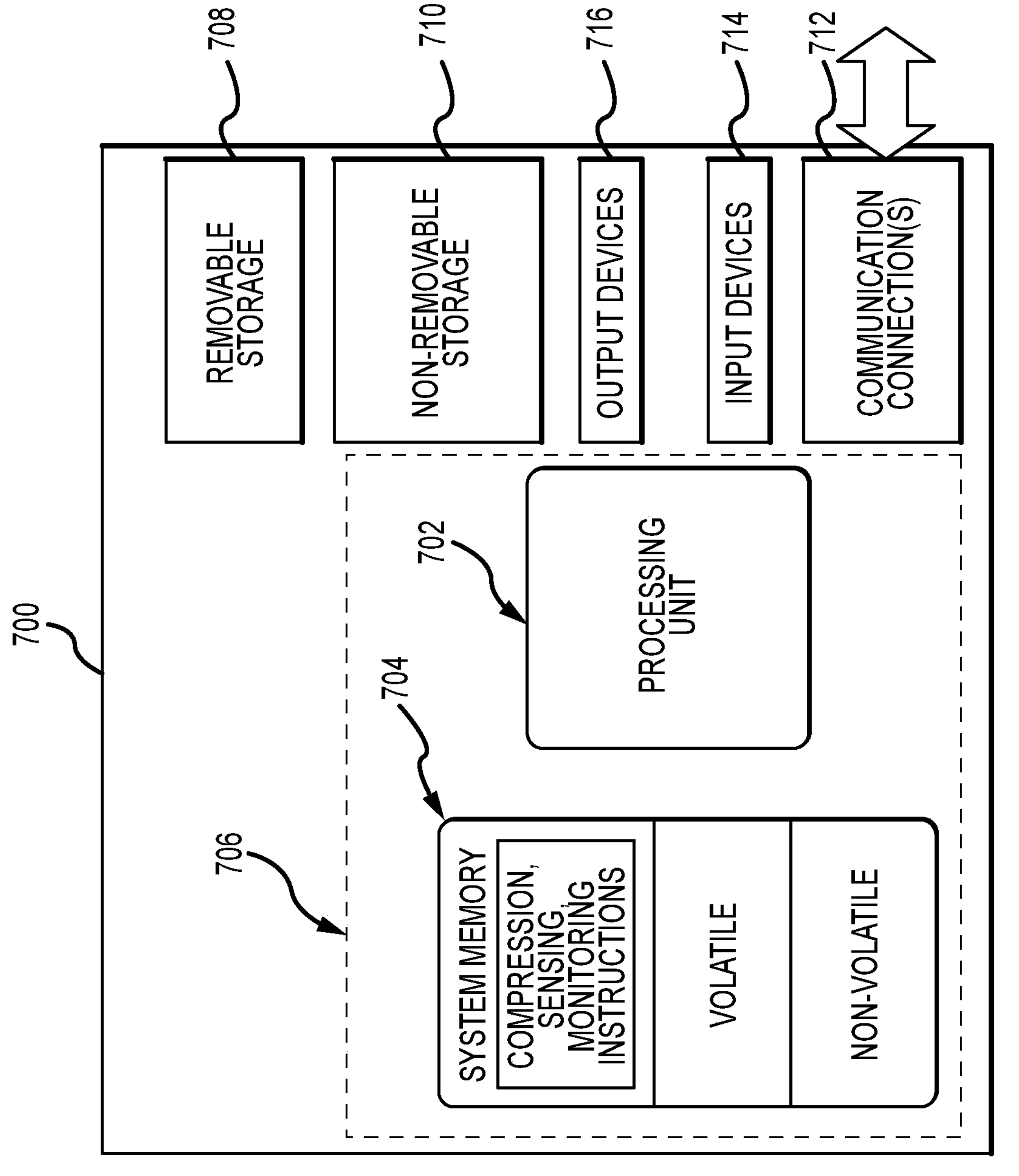
FIG. 7 depicts an example of a suitable operating environment in which one or more of the present examples can be implemented.

FIG. 7 illustrates one example of a suitable operating environment 700 in which one or more of the present examples can be implemented. This operating environment may be incorporated directly into the imaging systems disclosed herein, or may be incorporated into a computer system discrete from, but used to control, a the imaging systems described herein. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 700 typically includes at least one processing unit 702 and memory 704. Depending on the exact configuration and type of computing device, memory 704 (storing, among other things, instructions to perform the compression and sensing or monitoring methods disclosed herein) can be volatile (such as RAM), non-volatile (such as ROM, flash memory, etc.), or some combination of the two. This most basic configuration is illustrated in FIG. 7 by dashed line 706. Further, environment 700 can also include storage devices (removable, 708, and/or non-removable, 710) including, but not limited to, magnetic or optical disks or tape. Similarly, environment 700 can also have input device(s) 714 such as touch screens, keyboard, mouse, pen, voice input, etc., and/or output device(s) 716 such as a display, speakers, printer, etc. Also included in the environment can be one or more communication connections 712, such as LAN, WAN, point to point, Bluetooth, RF, etc.

Operating environment 700 typically includes at least some form of computer readable media. Computer readable media can be any available media that can be accessed by processing unit 702 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 700 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 700 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 700 is part of a network that stores data in remote storage media for use by the computer system 700.

Figure 8:
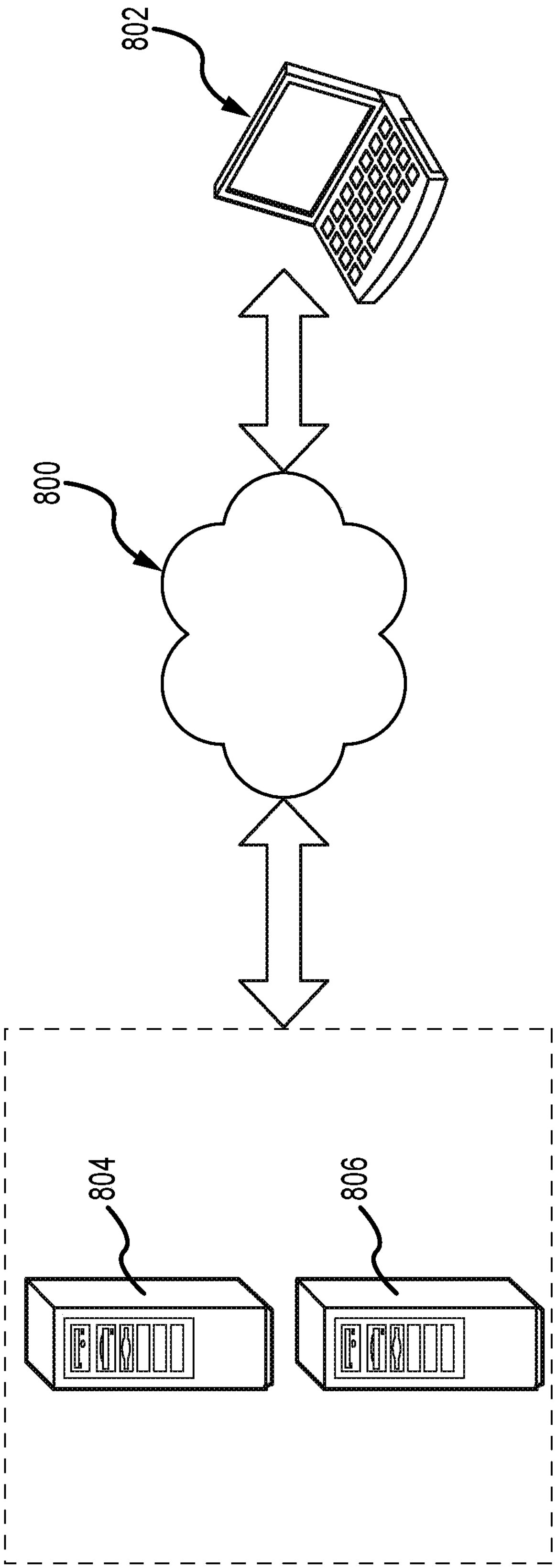
FIG. 8 depicts an example of a network in which the various systems and methods disclosed herein may operate.

FIG. 8 is an embodiment of a network 800 in which the various systems and methods disclosed herein may operate. In embodiments, a client device, such as client device 802, may communicate with one or more servers, such as servers 804 and 806, via a network 808. In embodiments, a client device may be a standalone imaging system (e.g., imaging system 80 depicted in FIG. 1A) that includes all the functionality described herein. The client device may also include or incorporate a laptop, a personal computer, a smart phone, a PDA, a netbook, or any other type of computing device, such as the computing device in FIG. 7. In examples, such a client device may be connected to an imaging system. In embodiments, servers 804 and 806 may also be any type of computing device, such as the computing device illustrated in FIG. 7. Network 808 may be any type of network capable of facilitating communications between the client device and one or more servers 804 and 806. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 804 may be employed to perform the systems and methods disclosed herein, such as the methods for imaging discussed herein. Client device 802 may interact with server 804 via network 808. In further embodiments, the client device 802 may also perform functionality disclosed herein, such as scanning and image processing, which can then be provided to servers 804 and/or 806.

In alternate embodiments, the methods and systems disclosed herein may be performed using a distributed computing network, or a cloud network. In such embodiments, the methods and systems disclosed herein may be performed by two or more servers, such as servers 804 and 806. Although a particular network embodiment is disclosed herein, one of skill in the art will appreciate that the systems and methods disclosed herein may be performed using other types of networks and/or network configurations.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of compressing a breast for an imaging procedure, the method comprising:

positioning a compression paddle in an initial position relative to the breast supported on a support platform, wherein the compression paddle includes a plurality of markers disposed thereon and the plurality of markers are Automatic Exposure Control (AEC) markers;

identifying an initial marker of the plurality of markers with a feature of the breast when the compression paddle is in the initial position;

based at least in part on the identified initial marker, automatically applying a compression force to the breast via the compression paddle to compress the breast between the compression paddle and the support platform; and acquiring one or more images while the breast is compressed.

2. The method of claim 1, wherein the initial position of the compression paddle is based on an initial contact point of the compression paddle relative to the breast as the compression paddle is advanced towards the support platform.

3. The method of claim 1, wherein the feature of the breast is at least one of a nipple or a skin line.

4. The method of claim 1, wherein the identified initial marker is based at least partially on a size of the breast.

5. The method of claim 1, wherein identifying the initial marker of the plurality of markers with the feature of the breast includes sensing, via a sensor, an alignment between the feature of the breast and the initial marker.

6. The method of claim 1, wherein automatically applying the compression force to the breast is based further on a target marker of the plurality of markers determined from the initial position and the initial marker.

7. The method of claim 1, wherein automatically applying the compression force to the breast includes comparing at least one of the initial marker and the initial position to a test dataset.

8. The method of claim 7, wherein the test dataset includes information obtained from prior compression of a plurality of breasts.

9. An imaging system comprising:

an x-ray source;

a support platform housing an x-ray detector;

a compression paddle disposed between the x-ray source and the support platform, the compression paddle comprising a plurality of markers disposed thereon and the plurality of markers are Automatic Exposure Control (AEC) markers;

at least one processing unit; and memory operatively in communication with the at least one processing unit, the memory storing instructions that, when executed by the at least one processing unit, are configured to cause the imaging system to perform a set of operations comprising:

position the compression paddle in an initial position relative to a breast supported on the support platform;

receive an identification of an initial marker of the plurality of markers with a feature of the breast when the compression paddle is in the initial position;

based at least in part on the identified initial marker, automatically apply a compression force to the breast via the compression paddle to compress the breast between the compression paddle and the support platform; and acquire one or more images while the breast is compressed.

10. The imaging system of claim 9, wherein the plurality of markers are positioned on the compression paddle at a plurality of distances from a leading edge of the compression paddle.

11. The imaging system of claim 9, wherein within the set of operations, the initial position of the compression paddle is based on an initial contact point of the compression paddle relative to the breast as the compression paddle is advanced towards the support platform.

12. The imaging system of claim 9, wherein within the set of operations, the feature of the breast is at least one of a nipple or a skin line.

13. The imaging system of claim 9, wherein within the set of operations, the identified initial marker is based at least partially on a size of the breast.

14. The imaging system of claim 9, further comprising a sensor, wherein within the set of operations, the identification of the initial marker of the plurality of markers with the feature of the breast is based on the sensor identifying an alignment between the feature of the breast and the initial marker.

15. The imaging system of claim 9, wherein within the set of operations, the automatic application of the compression force to the breast is based further on a target marker of the plurality of markers determined from the initial position and the initial marker.

16. The imaging system of claim 9, wherein within the set of operations, the automatic application of the compression force to the breast includes comparing at least one of the initial marker and the initial position to a test dataset.

17. The imaging system of claim 16, wherein the test dataset includes information obtained from prior compression of a plurality of breasts.

18. The imaging system of claim 9, wherein the imaging system is a mammography system, a tomosynthesis system, or a combo system.

* * * * *